United States Patent
Thiam et al.

(10) Patent No.: US 10,690,680 B2
(45) Date of Patent: Jun. 23, 2020

(54) METHOD FOR ANALYZING THE ACTIVITY OF AN ION CHANNEL

(71) Applicants: Paris Sciences Et Lettres - Quartier Latin, Paris (FR); Universite Paris Diderot Paris 7, Paris (FR); COMMISSARIAT A L'ENERGIE ATOMIQUE ET AUX ENERGIES ALTERNATIVES, Paris (FR)

(72) Inventors: Abdou Rachid Thiam, Choisy-le-roi (FR); Béatrice Schaack, Grenoble (FR)

(73) Assignees: Paris Sciences Et Lettres - Quartier Latin (FR); Universite Paris Diderot Paris 7 (FR); COMMISSARIAT A L'ENERGIE ATOMIQUE ET AUX ENERGIES ALTERNATIVES (FR)

( * ) Notice: Subject to any disclaimer, the term of this patent is extended or adjusted under 35 U.S.C. 154(b) by 246 days.

(21) Appl. No.: 15/776,685

(22) PCT Filed: Nov. 17, 2016

(86) PCT No.: PCT/EP2016/078013
§ 371 (c)(1),
(2) Date: May 16, 2018

(87) PCT Pub. No.: WO2017/085189
PCT Pub. Date: May 26, 2017

(65) Prior Publication Data
US 2018/0356430 A1 Dec. 13, 2018

(30) Foreign Application Priority Data
Nov. 17, 2015 (EP) .................................. 15306823

(51) Int. Cl.
*B01L 3/00* (2006.01)
*G01N 33/68* (2006.01)
*G01N 33/92* (2006.01)

(52) U.S. Cl.
CPC .... *G01N 33/6872* (2013.01); *B01L 3/502761* (2013.01); *G01N 33/92* (2013.01);
(Continued)

(58) Field of Classification Search
CPC ............... G01N 33/6872; G01N 33/92; G01N 2500/00; B01L 3/502761; B01L 2300/0867; B01L 2200/0652
See application file for complete search history.

(56) References Cited

U.S. PATENT DOCUMENTS 8,268,627 B2   9/2012  Bayley et al.
8,293,339 B2   10/2012 Faris et al.
(Continued)

FOREIGN PATENT DOCUMENTS

WO   2008012552 A1   1/2008

OTHER PUBLICATIONS

Barriga HM, Booth P, Haylock S, Bazin R, Templer RH, Ces O. Droplet interface bilayer reconstitution and activity measurement of the mechanosensitive channel of large conductance from *Escherichia coli*. Journal of the Royal Society Interface. Sep. 6, 2014;11(98):20140404; pp. 1-4.
(Continued)

*Primary Examiner* — Jennifer Wecker
*Assistant Examiner* — Michael Paul Shimek
(74) *Attorney, Agent, or Firm* — Lerner, David, Littenberg, Krumholz & Mentlik, LLP

(57) ABSTRACT

A method to analyze the activity of an ion channel comprising: providing in a hydrophobic medium a first droplet of an aqueous solution $AS_1$ comprising a concentration q of an
(Continued)

ion I with $c_1 \geq 0$, wherein the droplet is surrounded by a monolayer of amphiphilic molecules; providing in the hydrophobic medium a second droplet of an aqueous solution $AS_2$ comprising a concentration $c_2$ of the ion I with $c_2 \geq 0$, and $c_2 \neq c_1$, wherein the second droplet is surrounded by a monolayer of amphiphilic molecules further comprising the ion channels to an analyzed; bringing the first droplet and the second droplet into contact so as to form a bilayer of amphiphilic molecules, wherein the bilayer further comprises ion channels to be analyzed, and measuring the radius of the two droplets when they are brought into contact referred to as initial state; and maintaining the first droplet and the second droplet in contact until equilibrium is reached and measuring the radius of the two contacted droplets or determining the number of resulting droplet(s) at the equilibrium state, wherein the ion channel is inactive when the difference of the radius of at least one droplet between its initial state and its equilibrium state is at least 10% or when only one droplet is obtained at the equilibrium state.

20 Claims, 8 Drawing Sheets

(52) U.S. Cl.
CPC ............ *B01L 2200/0652* (2013.01); *B01L 2300/0867* (2013.01); *G01N 2500/00* (2013.01)

(56) References Cited

U.S. PATENT DOCUMENTS

| | | |
|---|---|---|
| 8,506,905 B2 | 8/2013 | Takeuchi et al. |
| 2012/0220481 A1 | 8/2012 | Wallace et al. |
| 2013/0147461 A1* | 6/2013 | Schmidt .................. C07F 9/22 324/76.11 |

OTHER PUBLICATIONS

Bayley H, Cronin B, Heron A, Holden MA, Hwang WL, Syeda R, Thompson J, Wallace M. Droplet interface bilayers. Molecular BioSystems. Dec. 2008;4(12):1191-208.
Schlicht B, Zagnoni M. Droplet-interface-bilayer assays in microlluidic passive networks. Scientific reports. Apr. 24, 2015;5:9951.
Schwarz D, Klammt C, Koglin A, Löhr F, Schneider B, Dötsch V, Bernhard F. Preparative scale cell-free expression systems: new tools for the large scale preparation of integral membrane proteins for functional and structural studies. Methods. Apr. 1, 2007;41(4):355-69.
Stanley CE, Elvira KS, Niu XZ, Gee AD, Ces O, Edel JB. A microfluidic approach for high-throughput droplet interface bilayer (DIB) formation. Chemical communications. Mar. 14, 2010;46(10):1620-2.
Thiam AR, Bremond N, Bibette J. From stability to permeability of adhesive emulsion bilayers. Langmuir. Apr. 4, 2012;28(15):6291-8.
Villar G, Heron AJ, Bayley H. Formation of droplet networks that function in aqueous environments. Nature nanotechnology. Dec. 2011;6(12):803.
Walsh E, Feuerborn A, Cook PR. Formation of droplet interface bilayers in a Teflon tube. Scientific reports. Sep. 29, 2016;6:34355.
International Search Report for PCT/EP2016/078013 dated Feb. 16, 2017.

* cited by examiner

METHOD FOR ANALYZING THE ACTIVITY OF AN ION CHANNEL

CROSS REFERENCE TO RELATED APPLICATIONS

The present application is a national phase entry under 35 U.S.C. § 371 of International Application No. PCT/EP2016/078013, filed Nov. 17, 2016, which claims priority from European Patent Application No. 15306823.4 filed Nov. 17, 2015, all of which are hereby incorporated herein by reference.

The present invention relates to a method for analyzing the activity of an ion channel which can be used for performing a high-throughput screening (HTS).

Ion channels are pore-forming membrane proteins which allow the flow of ions across the cell membrane. Ion channels are present in the membranes of all cells and constitute essential pharmacological drug targets in order to develop notably painkillers, anticonvulsants, antiarrhythmics, anticancer agents, epilepsy treatments, hearing disorder treatments, anti-inflammatory agents and neuromuscular blockers. They are generally specific to one type of ion.

The first methods developed to measure the activity of ion channels were based on live cell recordings. Overexpression of the ion channel of interest was often required for such approaches, which changes the cellular physiological state with unpredictable consequences on channel activity. This leads in many instances to toxicity for cell and their apoptosis. In these methods, the activity of the ion channels was measured mainly by patch-clamp or fluorescence.

The patch-clamp systems involve an electrophysiology-based measurement. An electrode is dipped into the cell and a reference electrode is outside in the solution containing the cell. When ions go through the channels, a current is generated across the membrane and is measured by the electrodes. If the channels are non-functional or blocked by compounds, no current will be recorded.

The fluorescence-based systems use ion-specific (or pH-dependent) fluorescent molecules. However, such ion-specific fluorescent molecules do not exist yet for all ions.

In order to overcome the drawbacks of the cell-based methods, cell-free methods have been developed still based on patch-clamp or fluorescence measures. In these cell-free methods, ion channels are expressed, purified and reconstituted in model membranes, such as droplet interface bilayer (DIB) (Bayley et al. 2008; Barriga et al. 2014; Villar et al. 2011; WO 2008/012552), possibly in a microfluidic platform (Schlicht and Zagnoni 2015).

Such a DIB can be notably produced at the interface between a droplet surrounded by a monolayer of amphiphilic molecules and a plane substrate covered also with a monolayer of amphiphilic molecules (US 2012/0220481) or between two droplets surrounded by a monolayer of amphiphilic molecules (U.S. Pat. Nos. 8,268,627; 8,293,339; 8,506,905). The lipids forming the membrane have to be carefully chosen in order to let the channel fold correctly.

In order to discover new pharmaceutics compounds targeting ion channels (such as painkillers, anticonvulsants, antiarrhythmics, anticancer agents, epilepsy, hearing disorder treatments, anti-inflammatory agents or neuromuscular blockers), it is useful to be able to screen chemical libraries of numerous compounds by automated, high-throughput assays.

However, the cell-based or cell-free methods known in the art have limitations that do not facilitate a high-throughput screening (HTS). Indeed, most current HTS methods involve compounds under flow, typically in microfluidic or millifluidic devices. Thus this precludes the use of patch-clamp methods due to the use of electrodes. The use of fluorescence-based methods is also not convenient due to the fact that a fluorescent smear is observed under flow of a fluorescent compound which basically generates noise and limits the readout.

One challenge to increase the discovery rate of drugs is to provide a method allowing measuring the passage of ions through membrane-imbedded channels in high throughput screening methods.

There exists thus a need for a method for analyzing ion channel activity applicable in a high throughput way with good readout.

The inventor of the present invention has thus developed an electrode and fluorescence-free method in which the ion channel activity is analysed by simple optical detection means such as a camera, notably in transmission light or brightfield, which overcome thus the problems of the prior art methods and allows thus the use of this method in high throughput screening.

The present invention relates thus to a method to analyze the activity of an ion channel (3) comprising the following steps:

(i) providing in a hydrophobic medium (1) a first droplet $D_1$ of an aqueous solution $AS_1$ comprising a concentration $c_1$ of an ion I with $c_1 \geq 0$, wherein the droplet $D_1$ is surrounded by a monolayer of amphiphilic molecules (2), (ii) providing in the said hydrophobic medium (1) a second droplet $D_2$ of an aqueous solution $AS_2$ comprising a concentration $c_2$ of the ion I with $c_2 \geq 0$ and $c_2 \neq c_1$, wherein the droplet $D_2$ is surrounded by a monolayer of amphiphilic molecules (2) further comprising the ion channels (3) to be analyzed, (iii) bringing the first droplet $D_1$ and the second droplet $D_2$ into contact so as to form a bilayer of amphiphilic molecules (2) in the contact area, wherein the bilayer of amphiphilic molecules (2) further comprises ion channels (3) to be analyzed, and (iv) measuring the size of the two contacted droplets or determining the number of resulting droplet(s) at the equilibrium.

Thus, the droplets $D_1$ and $D_2$ are maintained into contact until equilibrium is reached. The size of the two contacted droplets is also measured when the droplets are brought into contact so as to be able to compare the size/number of droplets when the droplets are brought into contact (initial state) and at the equilibrium (equilibrium state).

The invention will be described by way of example, with reference to the accompanying drawings.

Figure 1A:
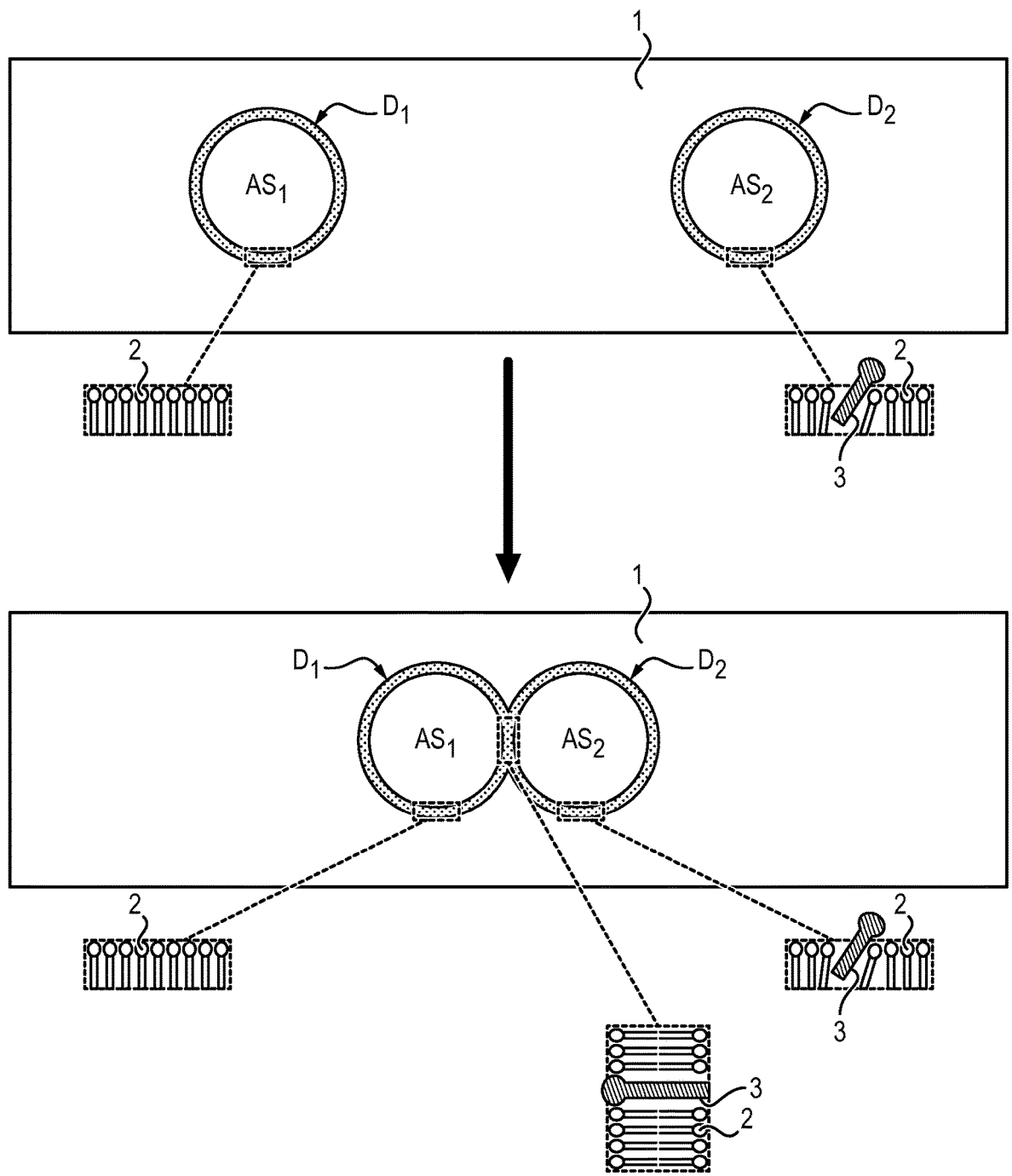
FIG. 1a illustrates step (iii) of the method according to the invention relative to the formation of the bilayer of amphiphilic molecules (2) comprising the ion channels (3) to be tested.
Figure 3:
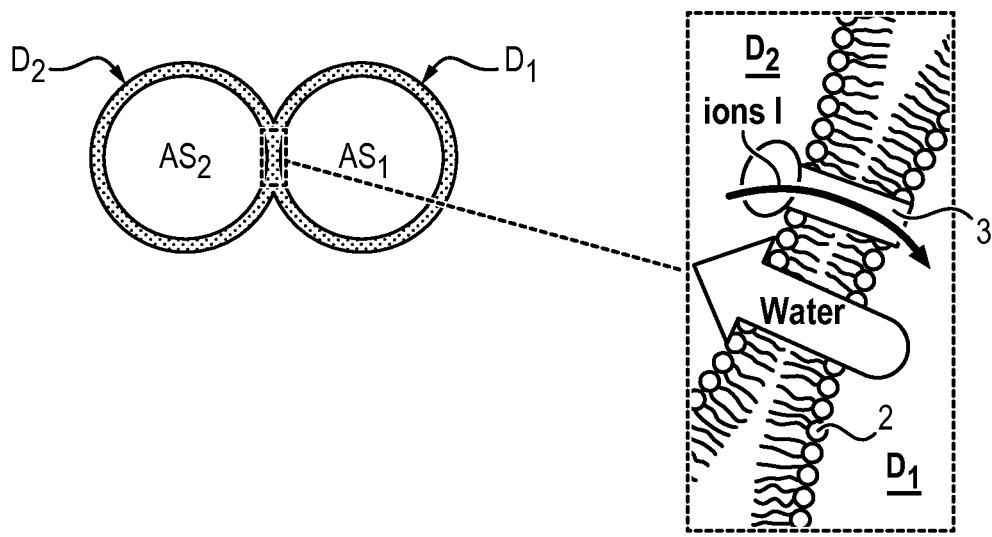
FIG. 3 illustrates the transfer of water and ions I through the bilayer of amphiphilic molecules (2) comprising the ion channels (3) to be tested in the case where $c_2 > c_1$ and where the ion channels (3) are active.

As demonstrated in the examples below, the bilayer of amphiphilic molecules (2) formed in step (iii) (see FIGS. 1a and 1b) mimics cell membrane and thus is permeable to water but impermeable to ions which can flow from a droplet to another one only through a specific ion channel (3). The ion is specific to an ion channel (3) (see FIG. 3).

Figure 2:
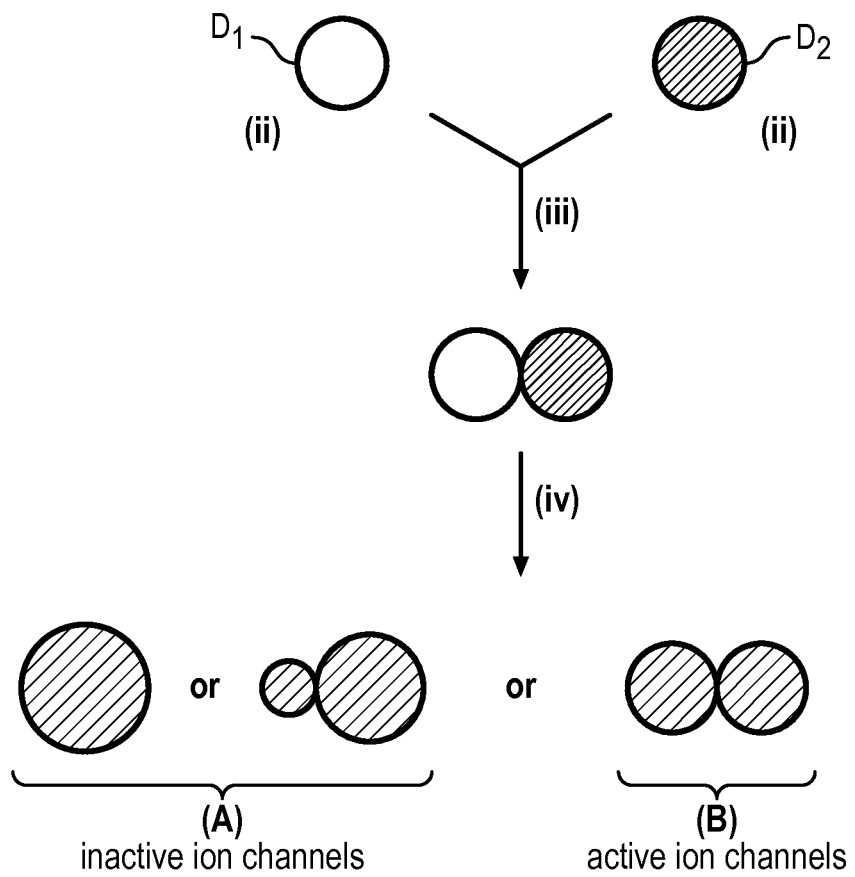
FIG. 2 illustrates the whole method according to the invention, only droplets $D_1$ and $D_2$ being represented.

Due to the difference of osmolarity between the two droplets, two situations can be observed after the contacting of the two droplets:

- if the ion channel (3) is inactive (for ex. due to the presence of a blocker) and does not allow the transport of ions I, ions I cannot flow through the ion channels (3) and thus water will traverse the membrane from the droplet having the lower concentration in ions I to the droplet having the higher concentrations in ions I in order to reach the same osmolarity between the two droplets which will lead to the reduction of the size of the droplet having the initial lower concentration in ions I and to the increase of the size of the droplet having the initial higher concentration in ions I and possibly to the merge of the two droplets so that only one droplet is obtained at the equilibrium (case (A) on FIG. 2);
- if the ion channel (3) is active and allows the transport of ions I, ions I can also flow through the ion channels (3) in order to reach the same osmolarity between the two droplets; the ion concentration and number of ion channels (3) in the bilayer can be adjusted so that the ion transfer rate through the ion channels is higher than the water transfer rate through the membrane, and thus the equilibrium will be mainly due to the ion transfer so that the size of the two droplets will not change substantially (case (B) on FIG. 2).

Consequently, if the size of the droplets is determined before being or when brought into contact (initial state), the measure of their size or the determination of the number of resulting droplet(s), after the droplets have been brought into contact and an equilibrium state has been reached, allows determining if the ion channel (3) is active or not. Such a measurement or determination can be performed by simple optical detection means such as a camera, notably in transmission light or brightfield, and more particularly a brightfield high-speed camera which is useable in a HTS method under flow of the droplets.

Figure 5:
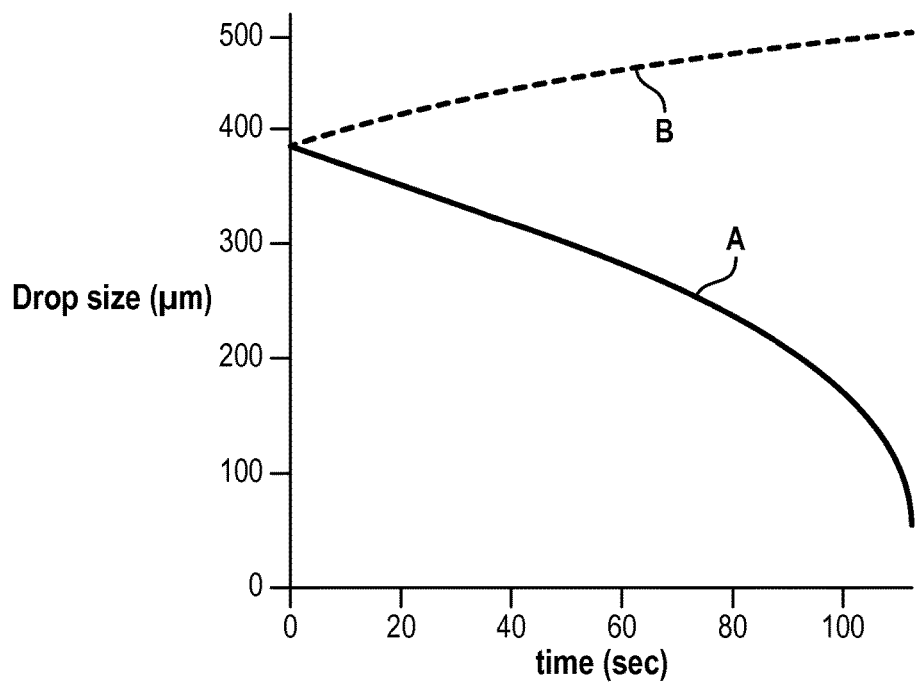
FIG. 5 illustrates a general and simulated case of the size change of the droplets in the case of inactive channels, using permeability values of droplet bilayers. The A curve relates to the droplet having the lower concentration of ions I, whereas the B curve relates to the droplet having the higher concentration of ions I.

By "equilibrium" is meant in the present invention a state where the size of the two droplets does not evolve anymore. Indeed, the flow of ions I and/or water through the bilayer membrane can take some time, in general few minutes, before reaching an equilibrium as illustrated on FIG. 5. It is thus important to wait for the equilibrium state, so that the size of the droplets does not evolve anymore, to analyse the difference of droplet size between the initial state and the equilibrium state.

The method according to the invention can be used to determine the ability of a substance (e.g. a chemical compound) to inactivate or not the ion channel (3). For that, the substance has to be present in one of aqueous solutions $AS_1$ and $AS_2$. Channel blockers, as well as channel regulators, can thus be screened.

If the substance is able to inactivate the ion channel (3), the ions I will be unable to flow through the ion channel (3) so that only water transfer will occur in order to equilibrate the osmolarity between the two droplets and a change of size of the two droplets (and possibly the merge of the two droplets) will be observed at the equilibrium.

On the contrary, if the substance is unable to inactivate the ion channel, the ions I will be capable of flowing through the ion channel (3) so that the size of the two droplets will not change substantially at the equilibrium.

Such a method can also be used for example to analyse an ion channel (3) in order to determine which kind of ions can flow through this ion channel (3).

However, this method will be mainly useful to determine the activity of a substance (as a blocker or a regulator) in relation to an ion channel (3).

A parameter to evaluate the size of a droplet is its radius (see FIG. 1b where $R_1$ represents the radius of the $D_1$ droplet and $R_2$ represents the radius of the $D_2$ droplet) which can be measured for example by a brightfield high-speed camera. Thus measuring the size of a droplet in the framework of the present invention can be performed by measuring its radius.

According to one embodiment, it will be considered that the ion channel (3) is inactive if only one droplet is obtained at equilibrium state or if there is a significant change of size of the droplets, e.g. the shrinking one which is the droplet having the initial lower concentration in ions I, and more particularly if the difference of the radius of at least one droplet (in particular the droplet having the initial lower concentration in ions I) between its initial state ($R_i$) and its equilibrium state ($R_e$) reached after being contacted with the other droplet is at least 10%, notably at least 20%, preferably at least 30%. This means that $|R_i-R_e|\times 100/R_i$ should be above 10%, notably above 20%, preferably above 30%.

According to another embodiment, it will be considered that the ion channel (3) is active if there is no significant change of size of the droplets, and more particularly if the difference of the radius of at least one droplet (in particular the droplet having the initial lower concentration in ions I) between its initial state ($R_i$) and its equilibrium state ($R_e$) after being contacted with the other droplet is less than 10%, notably less than 5%, preferably less than 3%. This means that $|R_i-R_e|\times 100/R_i$ should be inferior to 10%, notably inferior to 5%, preferably inferior to 3%.

According to another embodiment, it will be considered that the ion channel (3) is inactive if only one droplet is obtained at equilibrium state or if the difference of the radius of at least one droplet (in particular the droplet having the initial lower concentration in ions I) between its initial state ($R_i$) and its equilibrium state ($R_e$) reached after being contacted with the other droplet is at least 10% and that the ion channel (3) is active if the difference of the radius of at least one droplet (in particular the droplet having the initial lower concentration in ions I) between its initial state ($R_i$) and its equilibrium state ($R_e$) reached after being contacted with the other droplet is less than 10%.

Ion Channel (3):

A "ion channel" (3) is a pore-forming membrane protein which allows the flow of ions across the cell membrane. The ion channel (3) can be selective or not to an ion, the ion being commonly $Na^+$, $K^+$, $Ca^{2+}$, $H^+$ or $Cl^-$.

In the method according to the present invention, any ion channel (3) can be used. It can be notably a sodium channel, a potassium channel (e.g. Kv1.1 to Kv1.5 channel), a calcium channel, a proton channel or a chloride channel or a porine (e.g. α-hemolysin).

Consequently, the ion I will be in particular $Na^+$, $K^+$, $Ca^{2+}$, $H^+$ or $Cl^-$, more particularly $K^+$ or $Cl^-$. More particularly, the ion I is able to pass through the ion channel (3) to be analysed, i.e. that $Na^+$ will be used with a sodium channel, $K^+$ will be used with a potassium channel, $Ca^{2+}$ will be used with a calcium channel, $H^+$ will be used with a proton channel, and $Cl^-$ will be used with a chloride channel. However, if it is not known which kind of ions is able to go through the ion channel (3), it is possible to use the method according to the invention in order to test various ions and to determine the ions which are able to go through the ion channel (3).

It is also possible to perform the method using several different ion channels (3) in a same assay.

Hydrophobic Medium (1):

The "hydrophobic medium" (1) according to the invention is a medium which is not miscible with water and in particular with the aqueous solutions $AS_1$ and $AS_2$ mentioned previously.

Advantageously, it can be an oil such as a vegetable oil (e.g. soybean or mineral oil); triglycerides; silicone oil; a hydrocarbon; squalene or a mixture thereof.

"Triglycerides" (also called TG, triacylglycerol, TAG, or triacylglyceride) is an ester derived from glycerol and three fatty acids, which can be identical or different, notably identical. A triglyceride has more particularly the following formula (I):

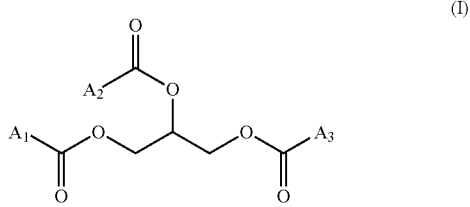

wherein $A_1$, $A_2$ and $A_3$, identical or different, notably identical, are a hydrocarbon chain of a fatty acid. The triglycerides used in the present invention can be in the form of a mixture of various triglycerides, such as triglycerides present in a vegetable oil (for ex. soybean oil).

In the context of the present invention, "fatty acid" refers to a linear, saturated or unsaturated carboxylic acid ($RCO_2H$) comprising from 4 to 30, such as from 6 to 30, notably from 8 to 28, in particular from 10 to 24, for example from 12 to 22 carbon atoms (including the carbon atom of the carboxylic acid function). It can be notably lauric acid, myristic acid, palmitic acid, staric acid, arachidic acid, myristoleic acid, myristelaidic acid, palmitoleic acid, palmitelaidic acid, oleic acid, elaidic acid, linoleic acid, linolenic acid, ecosenoic acid or arachidonic acid.

In the context of the present invention, "hydrocarbon chain of a fatty acid" refers to the hydrocarbon chain (R) linked to the acid function of the fatty acid ($RCO_2H$). R thus represents a linear, saturated or unsaturated hydrocarbon chain comprising from 3 to 29, such as from 5 to 29, notably from 7 to 27, in particular from 9 to 23, for example from 11 to 21 carbon atoms. It can be notably the hydrocarbon chain lauric acid, myristic acid, palmitic acid, staric acid, arachidic acid, myristoleic acid, myristelaidic acid, palmitoleic acid, palmitelaidic acid, oleic acid, elaidic acid, linoleic acid, linolenic acid, ecosenoic acid or arachidonic acid.

By "unsaturated" is meant in the present invention that the chain comprises one or several double bonds C=C, notably one to four, such as one, two or three.

The triglycerides can be in particular triglycerides of formula (I) with A1, A2 and A3, identical or different, representing a linear, saturated or unsaturated hydrocarbon chain comprising from 3 to 23, notably from 5 to 19 carbon atoms. The triglycerides can be present in the form of a mixture of various triglycerides, such as those present in a vegetable oil, for ex. soybean oil.

The hydrocarbon can be linear or branched, saturated or unsaturated (i.e. containing one or several double bond C=C). Advantageously, the hydrocarbon will contain at least 5 carbon atoms, notably at least 10 carbon atoms, in particular from 5 to 40 carbon atoms, such as from 10 to 30 carbon atoms provided that the hydrocarbon is liquid at the temperature at which the method is performed, typically room temperature (i.e. from 15 to 40° C., preferably from 20 to 30° C.). It can be notably pentane, decane, hexadecane or squalene, in particular squalene. It can be also in the form of a mixture of hydrocarbons such as a mineral oil.

Preferably, the hydrophobic medium (1) will comprise a mixture of triglycerides, notably present in a vegetable oil, such as soybean oil, and hydrocarbon such as squalene, preferably with an amount of hydrocarbon (e.g. squalene) in this mixture of at least 15% w/w. This kind of hydrophobic medium (1) allows improving the stability of the droplets and having a higher contact angle. Having higher contact angles is preferable as the bilayer area will be higher and thus so as the water/ion transfer rates. For example, for 250 μm-sized droplets, the few minutes time scale of the simulation for total water exchange in FIG. 5 was obtained by using a contact angle of 95°/2. Increasing that angle would speed up the exchange rate.

Amphiphilic Molecules (2):

An "amphiphilic molecule" (2) is a molecule comprising a hydrophilic part and a hydrophobic part.

The amphiphilic molecules (2) used in the present invention can be in particular lipids, such as phospholipids, glycolipids, cholesterol, and mixtures thereof which are the types of lipids commonly present in cell membranes. The lipids can have a natural or synthetic origin. More particularly, the amphiphilic molecules (2) can be phospholipids optionally in mixture with glycolipids and/or cholesterol. Advantageously, the amphiphilic molecules (2) will be phospholipids optionally in mixture with cholesterol. Preferably, the amphiphilic molecules (2) will be phospholipids.

"Phospholipids" are amphiphilic lipids comprising a phosphoric acid mono- or di-ester moiety as hydrophilic part. The phospholipids provide good stability to droplets, and thereupon to the bilayer, and, thanks to their charged headgroups, allow better incorporation of the ion channels (3). They can have a natural or synthetic origin. Preferably, synthetic phospholipids will be used. They can be a phosphatidylcholine (PC), a phosphatidylethanolamine (PE), a phosphatidylglycerol (PG), a phosphatidylserine (PS), a phosphatidic acid (PA), a phosphatidylinositol (PI), or a mixture thereof. These phospholipids have more particularly the following formula (II):

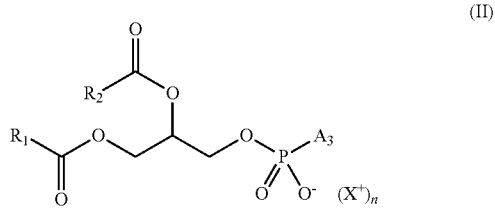

wherein:
- $X^+$ is a counterion, and more particularly a monovalent cation such as $Na^+$ or $NH_4^+$,
- n is 0 (i.e. $X^+$ is absent) or 1 (i.e. $X^+$ is present),
- $R_1$ and $R_2$, identical or different, preferably identical, are a hydrocarbon chain of a fatty acid (as defined above), and
- $R_3$ is:

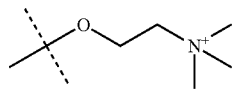

and n=0 (the phospholipid is thus a PC), or

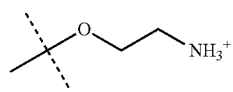

and n=0 (the phospholipid is thus a PE), or

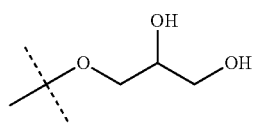

and n=1 (the phospholipid is thus a PG), or

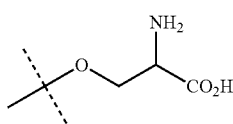

and n=1 (the phospholipid is thus a PS), or

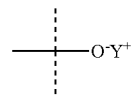

with n=1 and $Y^+$ is a counterion, and more particularly a monovalent cation such as $Na^+$ or $NH_4^+$ (the phospholipid is thus a PA), or

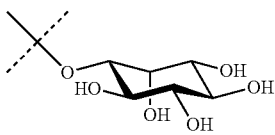

and n=1 (the phospholipid is thus a PI).

These phospholipids can be obtained from Avanti Polar Lipids.

Phospholipids formed with fatty acids having at least 12 carbon atoms (i.e. with a hydrocarbon chain having at least 11 carbon atoms) offer better stability to the droplets. Preferred phospholipids are those comprising a C18 fatty acid (i.e. with a hydrocarbon chain comprising 17 carbon atoms) such as oleic acid.

In particular the phospholipids will be a PC, a PE, a PS, a PG, or a mixture thereof, such as DOPC (dioleoylphosphatidylcholine), DPPC (dipalmitoylphosphatidylcholine), DOPE (dioleoylphosphatidylethanolamine), DOPS (dioleoylphosphatidylserine notably as a sodium salt), DOPG (dioleoylphosphatidylglycerone notably as a sodium salt) or a mixture thereof.

According to a particular embodiment, amphiphilic molecules (2) according to the present invention will be a PC, a PE or a mixture thereof, such as DOPC, DOPE or a mixture thereof. A mixture of DOPC and DOPE can be used advantageously with a molar ratio DOPC/DOPE ranging from 99/1 to 30/70. A mixture of DOPC and DOPE in a molar ratio DOPC/DOPE ranging from 70/30 to 50/50 gives a particular good stability to the droplets.

Droplets:

Advantageously, the droplets have a diameter comprised between 0.5 μm and 1000 μm, notably comprised between 20 μm and 500 μm, and preferably comprised between 50 μm and 200 μm. The droplets have thus substantially a spherical form.

The diameter of the droplets can be measured by a brightfield high-speed camera.

According to a preferred embodiment, the droplets $D_1$ and $D_2$ have substantially the same size, i.e. that the diameter $d_1$ of the droplet $D_1$ and the diameter $d_2$ of the droplet $D_2$ should advantageously satisfied the following equation: $|d_1-d_2|/(d_1+d_2) \leq 0.9$, notably $\leq 0.5$, preferably $\leq 0.2$.

The aqueous solutions $AS_1$ and $AS_2$ of the droplets $D_1$ and $D_2$ respectively contain advantageously a salt of ion I dissolved in water with respectively a concentration $c_1$ or $c_2$ as defined previously.

As indicated previously, the ion I can be more particularly $Na^+$, $K^+$, $Ca^{2+}$, $H^+$ or $Cl^-$. These ions I can be introduced in the aqueous solution in the form of a salt such as:
- for $Na^+$: NaCl, or NaOH,
- for $K^+$: KCl, KOH, $KCH_2COOH$, or $KSO_4$,
- for $Ca^{2+}$: $CaCl_2$, or $CaOH_2$,
- for $H^+$: HCl,
- for $Cl^-$: $MgCl_2$, $CaCl_2$, KCl, or NaCl.

Consequently, the aqueous solution will contain also counter-ions C of opposite charged in comparison to ions I. The nature of the counter-ion C will depend on the salt used to introduce the ion I in the aqueous solution.

When $c_1$, respectively $c_2$, is 0, the droplet aqueous solution $AS_1$, respectively $AS_2$, contains no ion I (or only traces).

When $c_1$ and $c_2$ are different from 0, they are advantageously substantially different, notably as defined in the following equation:

$$|c_1-c_2|/(c_1+c_2)>0.1, \text{ notably } \geq 0.5, \text{ preferably } \geq 0.9.$$

According to a preferred embodiment the higher concentration of $c_1$ and $c_2$ is comprised between 1 mM and 1 M, notably between 100 mM and 800 mM, preferably between 300 mM and 700 mM.

According to another embodiment, one of the concentrations $c_1$ and $c_2$ is 0 and the other is different from 0, and is advantageously comprised between 1 mM and 1 M, notably between 100 mM and 800 mM, preferably between 300 mM and 700 mM. In particular, $c_1=0$.

Advantageously, the aqueous solution $AS_1$ and/or $AS_2$, preferably $AS_2$, could also contain a substance (such as a chemical compound) to be tested for its blocking activity of the ion channel (3) or a dye substance (for ex. red rhodamine dye) in order to be able to visually distinguish the droplets $AS_2$ from the droplets $AS_1$.

Figure 1B:
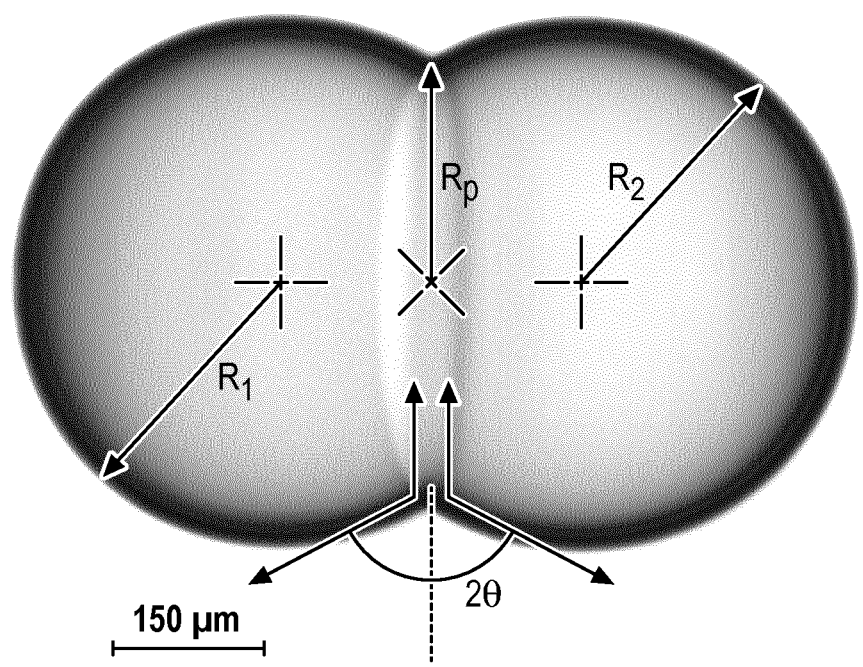
FIG. 1b illustrates the obtained bilayer of amphiphilic molecules (2) comprising the ion channels (3) between droplets $D_1$ and $D_2$.

FIG. 1b represents $D_1$ and $D_2$ droplets after contacting, forming thus a bilayer of amphiphilic molecules (2) containing also ion channels (3). The main parameters of this pair of droplets are: $R_1=d_1/2$ which is the radius of the $D_1$ droplet; $R_2=d_2/2$ which is the radius of the $D_2$ droplet; $R_p$ which is the radius of the bilayer area; and θ which is the contact angle and is calculated as follows: $2\theta=\sin^{-1}(R_p/R_1)+\sin^{-1}(R_p/R_2)$.

The various radii ($R_p$, $R_1$ and $R_2$) can be measured by a brightfield high-speed camera.

Advantageously, the contact angle θ is comprised between 1 and 90°, notably between 30 and 90°, preferably between 50 and 90°.

As indicated previously, having higher contact angles is advantageous as the bilayer area will be higher and thus the water/ion transfer rates will be also higher. Higher contact angles allow thus speeding up the exchange rate.

Step (i):

The droplet $D_1$ surrounded by a monolayer of amphiphilic molecules (2) can be provided by forming a droplet of the aqueous solution $AS_1$ in the hydrophobic medium (1) which contains the amphiphilic molecules (2). The amphiphilic molecules (2) will then spontaneously place themselves at the interface between the aqueous droplet and the hydrophobic medium (1).

Preferably, in this step, the volume of the hydrophobic medium (1) is at least twice the volume of the aqueous solution $AS_1$ used to form the droplets.

The concentration of the amphiphilic molecules (2) in the hydrophobic medium (1) is advantageously at least 0.025% (w/w).

Step (ii):

The method to provide a droplet $D_2$ surrounded by a monolayer of amphiphilic molecules (2) comprising the ion channels (3) will depend if the ion channel (3) is used in liposomes or not. Indeed, if the ion channels (3) are not soluble in the aqueous solution $AS_2$, it will be necessary to use it in liposomes. Indeed, liposomes will guarantee the safe carriage of the protein (ion channel) without its denaturation. Furthermore, the liposome protein content can be relocated into the oil/water surface at the interface of the droplets with the hydrophobic medium.

Should the ion channel (3) not be contained in a liposome but surrounded by amphiphilic molecules, it is soluble in the aqueous solution $AS_2$. The $D_2$ droplet surrounded by a monolayer of amphiphilic molecules (2) comprising the ion channels (3) to be analyzed can be provided by forming a droplet of the aqueous solution $AS_2$ which contains also the ion channels (3) in the hydrophobic medium (1) which contains the amphiphilic molecules (2). The amphiphilic molecules (2) will then spontaneously place themselves at the interface between the aqueous droplet and the hydrophobic medium (1) to form a monolayer of amphiphilic molecules (2) around the $D_2$ droplet. Within the $D_2$ droplet surrounded by the monolayer of amphiphilic molecules (2), the ion channel (3) tends to migrate and associate with the hydrophobic medium (1) forming the monolayer of amphiphilic molecules (2) and ion channels (3) around the droplet.

Should the ion channel (3) be contained in a liposome (forming thus proteo-liposomes), the droplet of the aqueous solution $AS_2$ which contains also the ion channels (3) in proteo-liposomes will be formed in the hydrophobic medium (1) containing no amphiphilic molecule (2). The droplet thus formed is then shaken (notably vortexed or by flowing the droplets $D_2$ in a zig-zag array in microfluidics) in order to explode the proteo-liposomes on the water-hydrophobic medium (1) interface so that to place the ion channels (3) at the water-hydrophobic medium (1) interface. Then amphiphilic molecules (2) are added to the hydrophobic medium (1) in order to form spontaneously the monolayer of amphiphilic molecules (2) which contains also the ion channels (3) to be analysed around the droplet.

Preferably, in this step, the volume of the hydrophobic medium (1) is at least twice the volume of the aqueous solution $AS_2$ used to form the droplets.

The concentration of the amphiphilic molecules (2) in the hydrophobic medium (1) is advantageously at least 0.025% (w/w).

There should be enough ion channels (3) associated to the monolayer surrounding the droplet $D_2$ to allow their recruitment in the bilayer, with keeping their functionality, and a sufficient flow of ions I through these ion channels (3). For example, the monolayer formed around the droplet $D_2$ can contain at least one ion channel (3) for 100 millions, notably 80 millions, preferably 50 millions, of amphiphilic molecules (2).

Steps (iii) and (iv):

The two droplets $D_1$ and $D_2$ are brought into contact by any means (for ex. by mixing binary droplets or by changing the flow rate in microfluidics) used in the art. Generally, droplets $D_1$ and $D_2$ are formed separately in a hydrophobic medium (1) before merging together the two hydrophobic media (1) containing respectively droplets $D_1$ and $D_2$.

Since there exists a difference of osmolarity between the two droplets due to the difference between $c_1$ and $c_2$, a flux of water and/or of ions I (if the ion channels (3) are active in this last case) will occur once the two droplets are brought into contact in order to establish equilibrium by reaching the same osmolarity. Thus, two situations can be observed:

if the ion channel (3) is inactive (for ex. due to the presence of a blocker) and does not allow the transport of ions I, ions I cannot flow through the ion channels (3) and thus water will traverse the membrane from the droplet having the lower concentration in ions I to the droplet having the higher concentrations in ions I in order to equilibrate osmolarity between the two droplets which will lead to the reduction of the size of the droplet having the initial lower concentration in ions I and to increase the size of the droplet having the initial higher concentration in ions I and possibly to the merge of the two droplets to obtain at the end only one droplet;

if the ion channel (3) is active and allows the transport of ions I, ions I will flow through the ion channels (3) in order to equilibrate the osmolarity between the two droplets which will not change the size of the two droplets.

Consequently, the measurement of the size of the droplets at different time points or at equilibrium by determining droplets contour variation, or the determinations of the number of final droplet(s) (one big droplet or two droplets) at the equilibrium allows determining if the ion channel (3) is active or not. Such a measurement or determination can be performed by an optical detection system such as a camera, notably in transmission light or brightfield, and more particularly a brightfield high-speed camera, notably by measuring the radius of the droplets.

In particular, the size of the contacted droplets will be measured when the two droplets are brought into contact (initial state) and at the equilibrium (or the number of droplets will be determined if there remains only one droplet at the equilibrium) and these two measures will be compared.

According to one embodiment, it will be considered that the ion channel (3) is inactive if only one droplet is obtained at equilibrium state or if there is a significant change of size of the droplets, e.g. the shrinking one which is the droplet having the initial lower concentration in ions I, and more particularly if the difference of the radius of at least one droplet (in particular the droplet having the initial lower concentration in ions I) between its initial state ($R_i$) and its equilibrium state ($R_e$) reached after being contacted with the other droplet is at least 10%, notably at least 20%, preferably at least 30%. This means that $IR_i-R_eIx100/R_i$ should be above 10%, notably above 20%, preferably above 30%.

According to another embodiment, it will be considered that the ion channel (3) is active if there is no significant change of size of the droplets, and more particularly if the difference of the radius of at least one droplet (in particular the droplet having the initial lower concentration in ions I) between its initial state ($R_i$) and its equilibrium state ($R_e$) after being contacted with the other droplet is less than 10%, notably less than 5%, preferably less than 3%. This means that $IR_i-R_eIx100/R_i$ should be inferior to 10%, notably inferior to 5%, preferably inferior to 3%.

According to another embodiment, it will be considered that the ion channel (3) is inactive if only one droplet is obtained at equilibrium state or if the difference of the radius of at least one droplet (in particular the droplet having the initial lower concentration in ions I) between its initial state ($R_i$) and its equilibrium state ($R_e$) reached after being contacted with the other droplet is at least 10% and that the ion channel (3) is active if the difference of the radius of at least one droplet (in particular the droplet having the initial lower concentration in ions I) between its initial state ($R_i$) and its equilibrium state ($R_e$) reached after being contacted with the other droplet is less than 10%.

According to yet another embodiment, if we choose values of concentrations $c_1$ and $c_2$ sufficiently different (for ex. c2>>c1–0 mM, the higher the difference the faster the equilibrium time; however, if is it too high, bilayers may not be sufficiently stable; the range of concentration is preferably as aforementioned) to lead necessarily to the merge of the two droplets at the equilibrium when the ion channels (3) are inactive, then:

the obtaining of one droplet at the equilibrium will mean that the ion channels (3) are inactive, whereas the obtaining of two droplets at the equilibrium will mean that the ion channels (3) are active.

In this case, the determination of the activity of the ion channels (3) to be analyzed can be performed by a simple binary readout (one big droplet or two droplets at the equilibrium) by means of an optical detection system, such as a camera, notably in transmission light or brightfield, and more particularly a brightfield high-speed camera.

The time necessary to reach the equilibrium will depend on various parameters such as the initial size of the droplets $D_1$ and $D_2$, the contact angle, the concentrations $c_1$ and $c_2$, the nature of the ion channel (3) to be analyzed, the number of ion channels (3) in the bilayer, etc. However, for droplets having an initial size comprised between 100 μm and 1000 μm, we can estimate that the equilibrium should be reached after 1 min to 30 min.

Microfluidic Device:

Due to the simple way for determining the activity of the ion channels (3) by an optical detection system, such as a camera, notably in transmission light or brightfield, and more particularly a brightfield high-speed camera, which can be easily used in an automated way, the method according to the invention can be performed in high-throughput, in particular in a HTS method.

Figure 6A:
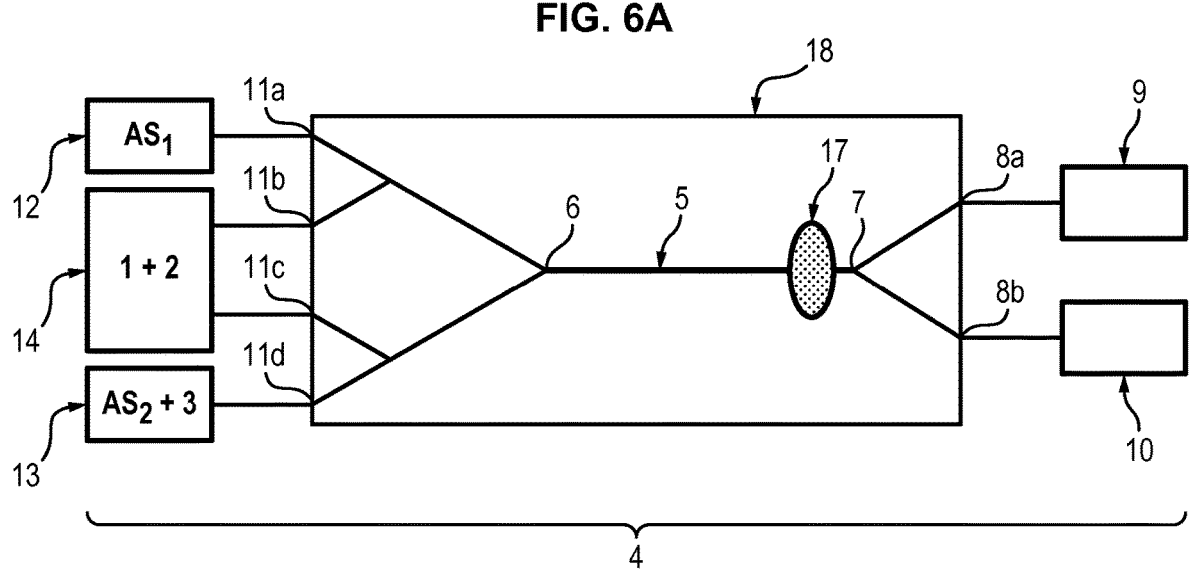
FIGS. 6A, 6B and 6C illustrate various embodiments of a microfluidic analysis system (4) according to the invention useful to perform the method according to the invention in a high-throughput manner (op. means optionally).
Figure 6B:
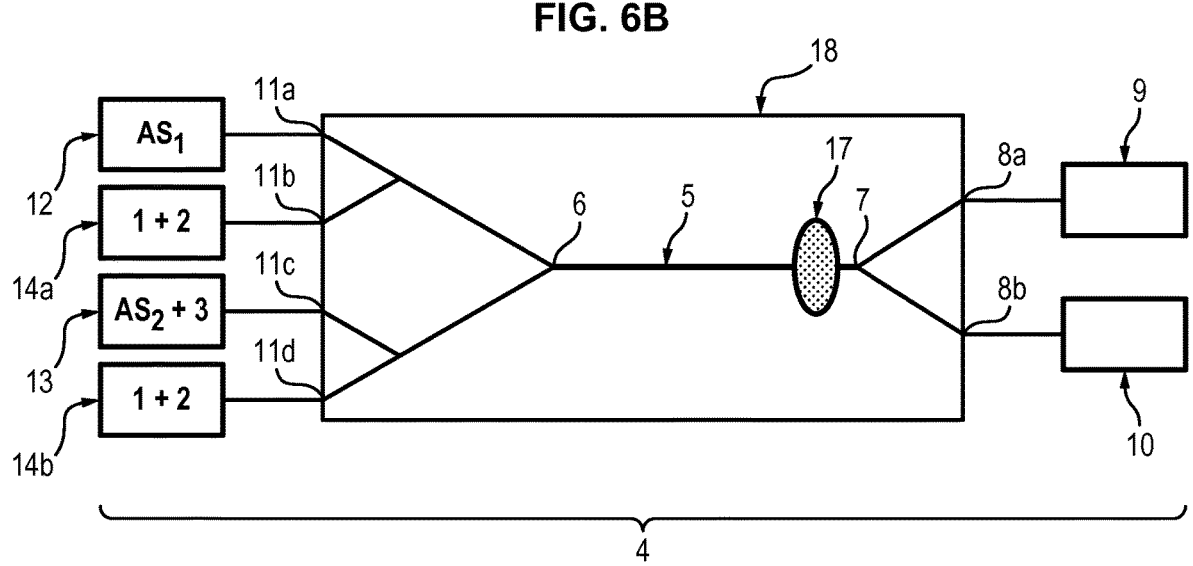
Figure 6C:
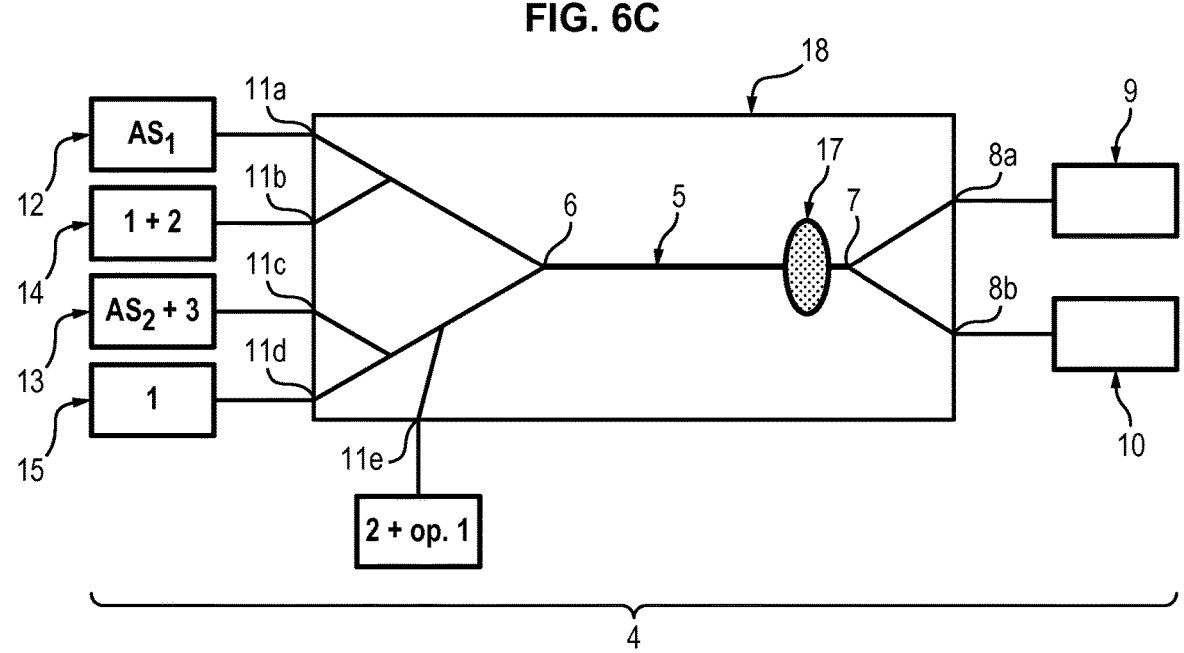

Such a high-throughput method can be performed by the use of a microfluidic analysis system (4). Such an analysis system (4) could comprise:

a microfluidic device (18) comprising:

a main microfluidic channel (5) comprising one inlet (6) and one outlet (7), through which alternate droplets $D_1$ and $D_2$ can flow in the hydrophobic medium (1) from the inlet (6) to the outlet (7) of the channel, at least two outlets (8a,8b) connected to the outlet (7) of the main microfluidic channel (5) and wherein:

the first outlet (8a) of the microfluidic device (18) is further connected to a first receiver container (9) intended to receive the droplets analyzed as containing active ion channels (3), and the second outlet (8b) of the microfluidic device (18) is further connected to a second receiver container (10) intended to receive the droplets analyzed as containing inactive ion channels (3), at least four inlets (11a,11b,11c,11d) connected to the inlet (6) of the main microfluidic channel (5) and wherein:

the first two inlets (11a,11b) of the microfluidic device (18) are further connected respectively to a reservoir (12) intended to contain the aqueous solution $AS_1$ and to a reservoir (14) intended to contain the hydrophobic medium (1) and the amphiphilic molecules (2), and the last two inlets (11c,11d) are further connected respectively to a reservoir (13) intended to contain the aqueous solution $AS_2$ and the ion channels (3) optionally present in liposomes and to a reservoir (14 or 15) intended to contain the hydrophobic medium (1) and optionally the amphiphilic molecules (2), wherein, when the ion channels (3) are present in the aqueous solution $AS_2$ in liposomes, the microfluidic device (18) comprises a fifth inlet (11e) connected to the inlet (6) of the main microfluidic channel (5) and to a reservoir (16) intended to contain the amphiphilic molecules (2) and optionally the hydrophobic medium (1), at least three reservoirs adapted for containing respectively (i) the aqueous solution $AS_1$ (reservoir (12)), (ii) the aqueous solution $AS_2$ and the ion channels (3) optionally present in liposomes (reservoir (13)), and (iii) the hydrophobic medium (1) and/or the amphiphilic molecules (2) (reservoir(s) (14),(15),(16)) (wherein, according to the embodiments, there can be for example (a) one reservoir (14) for the mixture hydrophobic medium (1)/amphiphilic molecules (2) (see FIG. 6A); (b) two reservoirs (14a,14b) for the mixture hydrophobic medium (1)/amphiphilic molecules (2) (see FIG. 6B); or (c) one reservoir (14) for the mixture hydrophobic medium (1)/amphiphilic molecules (2), one reservoir (15) for the hydrophobic medium (1) alone, and one reservoir (16) for the amphiphilic molecules (2) optionally in mixture with the hydrophobic medium (1) (see FIG. 6C)), at least two receiver containers (9,10) adapted for receiving respectively (i) the droplets analyzed as containing active ion channels (3) (reservoir (9)), and (ii) the droplets analyzed as containing inactive ion channels (3) (reservoir (10)) (these droplets being collected with the surrounding hydrophobic medium (1) and amphiphilic molecules (2) in both cases), and a detection device (17) placed at the end of the main microfluidic channel (5), such as a camera, notably in transmission light or brightfield, and more particularly a brightfield high-speed camera.

By "microfluidic channel" (5) is meant in the present invention a channel having a cross section which has dimensions in the micrometer range. Typically, the microfluidic channel (5) will have a width and a depth comprised between 10 μm and 1000 μm, in particular between 10 μm and 400 μm, notably between 10 μm and 250 μm, preferably between 10 and 100 μm or between 150 and 250 μm. However, the length of the microfluidic channel (5) can be in the centimeter, decimeter or even meter range.

Droplets $D_1$ are formed in the microfluidic device (18) by any means from the hydrophobic medium (1) containing the amphiphilic molecules (2) and the aqueous solution $AS_1$ which enter the microfluidic device (18) through its two first inlets (11a,11b). Once formed, droplets $D_1$ flow in the hydrophobic medium (1) until the inlet (6) of the microfluidic channel (5). Droplets $D_1$ can be formed for example by shearing a flow of aqueous solution $AS_1$ with two flows of hydrophobic medium (1) containing the amphiphilic molecules (2), method well-known to the one skilled in the art. The monolayer of amphiphilic molecules (2) is then formed spontaneously around the droplets $D_1$.

Droplets $D_2$ are formed in a similar way as for droplets $D_2$. Once formed, droplets $D_2$ flow in the hydrophobic medium (1) until the inlet (6) of the microfluidic channel (5).

When the ion channels (3) are not present in liposomes (because they are soluble in aqueous solution $AS_2$ when surrounded by amphiphilic molecules), the droplets $D_2$ will be formed in the microfluidic device (18) by any means from the hydrophobic medium (1) containing the amphiphilic molecules (2) and the aqueous solution $AS_2$ further containing the ion channels (3) which enter the microfluidic device (18) through its two last inlets (11c,11d). Droplets $D_2$ can be formed also by shearing a flow of aqueous solution $AS_2$ further containing the ion channels (3) with two flows of hydrophobic medium (1) containing the amphiphilic molecules (2), method well-known to the one skilled in the art. The monolayer of amphiphilic molecules (2) associated to ion channels (3) is then formed spontaneously around the droplets $D_2$.

When the ion channels (3) are present in liposomes, the droplets $D_2$ will be formed in the microfluidic device (18) by any means from the hydrophobic medium (1) (containing no amphiphilic molecule (2)) and the aqueous solution $AS_2$ further containing the ion channels (3) which enter the microfluidic device (18) through two inlets (11c,11d). Droplets $D_2$ can be formed notably by shearing a flow of aqueous solution $AS_2$ further containing the ion channels (3) with two flows of hydrophobic medium (1) (containing no amphiphilic molecule (2)). Once the droplets $D_2$ are formed, they need to be shaken in order to explode the liposomes containing the ion channels (3) on the water-hydrophobic medium interface so that to place the ion channels (3) at the water-hydrophobic medium interface. For that, droplets $D_2$ can flow in a zig-zag array (notably a zig-zag microfluidic channel). After this step, amphiphilic molecules (2) (optionally in mixture with hydrophobic medium (1)) have to be added to the flow of hydrophobic medium (1) containing the droplets $D_2$ by another inlet (11e) of the microfluidic device. This allows the spontaneous formation of the monolayer of amphiphilic molecules (2) associated to ion channels (3) around the droplets $D_2$.

Advantageously, droplets $D_1$ and $D_2$ enter alternately the main microfluidic channel (5) through its inlet (6) and flow through this main microfluidic channel (5) from its inlet (6) to its outlet (7). Pairs of droplets $D_1$ and $D_2$ are brought into contact in this main microfluidic channel (5), for ex. by varying the pressure/flow rate in the microfluidic channel (5), so as to form the bilayer of amphiphilic molecules (2) containing the ion channels (3). Advantageously, the main microfluidic channel (5) will be linear.

The pairs of droplets $D_1$ and $D_2$ will flow through this main microfluidic channel (5) until the end of this microfluidic channel (5) where the size or number, preferably the number, of the "pair of droplets" will be analyzed by the detection device (17). The main microfluidic channel (5) should thus be sufficiently long so that equilibrium is reached when the "pair of droplets" arrived at the end of main microfluidic channel (5) to be analyzed by the detection device (17). A valve controlled by the detection device (17) can be present at the end of the main microfluidic channel (5). Depending on the size or number of the "pair of droplets", the detection device (17) will move the valve so that the droplets containing active ion channels (3) are moved towards the first receiver container (9) through the first outlet (8a) of the microfluidic device (18) and the droplets containing inactive ion channels (3) are moved towards the second receiver container (10) through the second outlet (8b) of the microfluidic device (18).

The detection device (18) comprises advantageously an optical detection system, such as a camera, notably in transmission light or brightfield, and more particularly a brightfield high-speed camera. It can be more particularly a basic sorting device having ideally an optical detection system, such as a camera, notably a high speed camera, and more particularly a brightfield high-speed camera, coupled with a software capable of analysing the droplet size/number to provide a binary value allowing for example moving a valve in the required position in order to direct the "pair of droplets" in the appropriate receive container (9,10). For instance, we will use a microfluidic valve which will be only timely opened for allowing the sorting of a droplet that has been positive for ion channel activity by the software; the software would for example send a 1 message to the valve for opening and a 0 message for closing; sorted droplets will simply be collected after the valve where the valve signal will be 1.

Such a microfluidic analysis system (4) will allow forming and testing numerous pairs of droplets with an automated treatment of the results. In order to perform HTS, it will be possible to introduce various substances to be analyzed in aqueous solutions $S_1$ and/or $S_2$. The droplets containing inactive ion channels (3) collected at the second outlet (8b) will correspond to the droplets containing substances capable to block the ion channels (3). An analysis of these droplets, notably by mass spectrometry (possibly after HPLC to separate the various substances), will allow the identification of the active substances.

The present invention will be illustrated by the following non-limiting examples.

EXAMPLES

1. Example with No Ion Channel Illustrative of the Presence of Inactive Ion Channels Two water-in-oil emulsion droplets (Oil/Water (8/1, v/v) were separately formed before being mixed and vortexed.

The first class of water droplets contained 0 mM KCl and is formed in the oil phase (soybean oil/squalene (50/50 w/w)) containing phospholipids from Avanti Polar Lipids (DOPC/DOPE (70/30 mol/mol) at 0.2% w/w relative to the oil), which decorated the droplet interface. Phospholipids (PLs) in chloroform were placed in a glass vial so as to evaporate under vacuum the chloroform; after they were dried and oil is added in a sufficient amount to reach the target concentration; the mixture is thoroughly mixed—e.g. 20 µl of PLs at 25 mg/ml were dried and 250 mg of the oil was added to reach 0.2%. The different solutions (aqueous and oil phases) were then mixed and vortexed (50 µL of the aqueous phase+350 µL of the oil phase) to generate population $D_1$ of droplets.

The second class of aqueous droplets containing 0.5 M KCl or 0.25 M $MgCl_2$ (and red rhodamine dye (for eye visualization) and differentiation from the $D_1$ class of droplets) (the previous droplet fabrication procedure was repeated with 0.5 M KCl or 0.25 M $MgCl_2$ and 0.01% w/w of red rhodamine dye in the water in place of water) was formed in the oil devoid of phospholipids (50 µL of the aqueous phase+350 µL of the oil phase) in order to reach a population $D_2$ of droplets.

The two emulsions were then mixed together. The equilibrium of red and white droplets (i.e. $D_2$ and $D_1$ droplets respectively) forming DIBs was then followed over time. White droplets of lower osmolarity completely transferred their water content to the red droplets of higher osmolarity after 30 min contact.

Figure 8A:
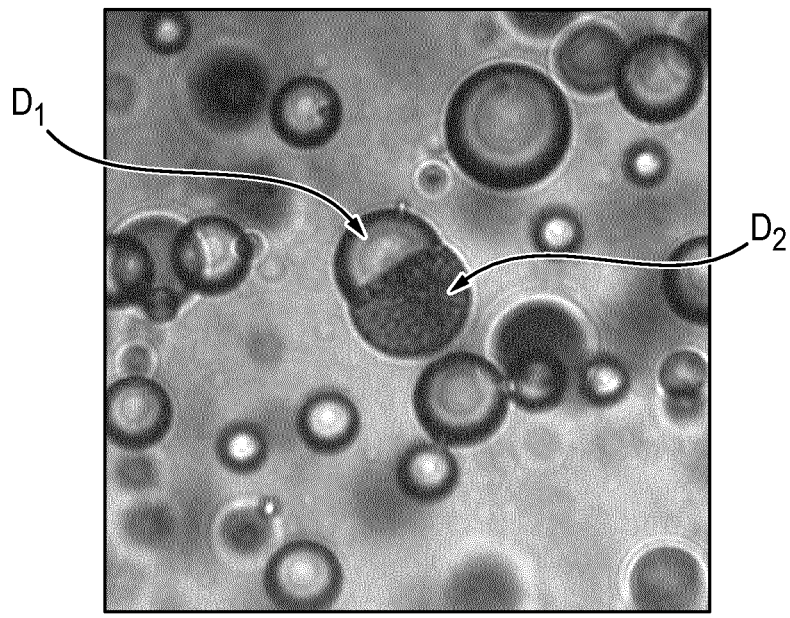
FIGS. 8a and 8b illustrate the evolution of the droplets $D_1$ and $D_2$ during time, i.e. at the beginning of the experiment (FIG. 8a) and at the end (FIG. 8b) when equilibrium has been reached.
Figure 8B:
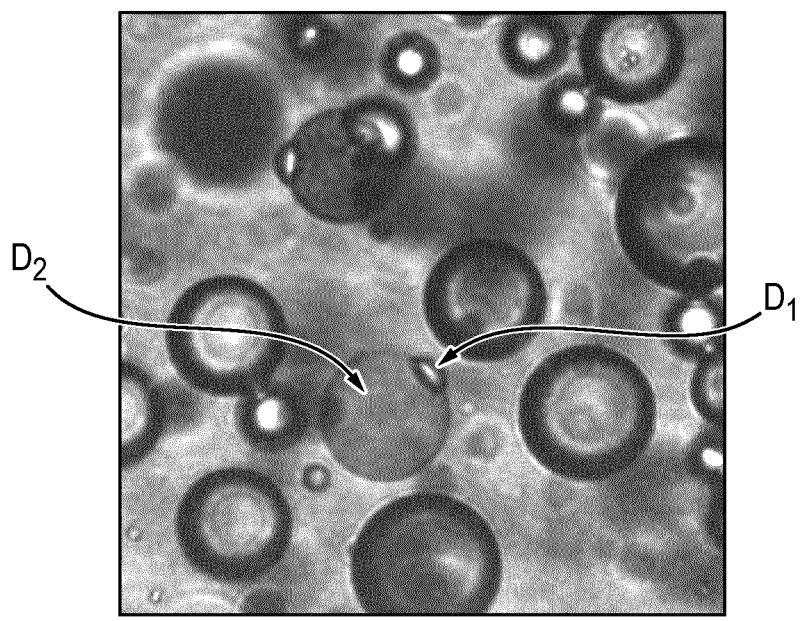

The evolution of the droplets $D_1$ and $D_2$ during time is illustrated by FIG. 8a (photograph taken at the beginning of the experiment) and FIG. 8b (photograph taken at the end of the experiment when equilibrium has been reached).

Figure 4A:
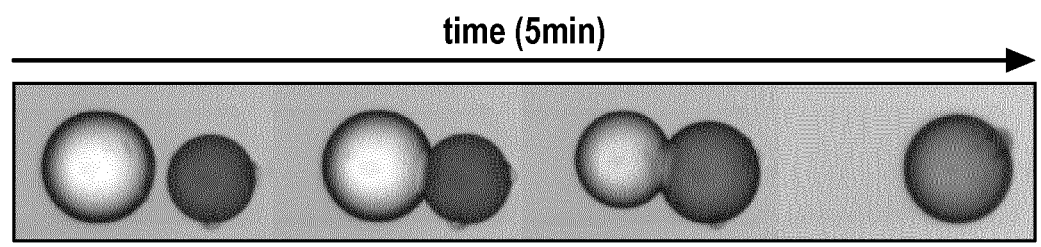
FIG. 4a illustrates the evolution of the droplets $D_1$ and $D_2$ during time (on a period of 5 min) in the case where the ion channels (3) are inactive. The starting light grey droplet contains no ions I, whereas the starting dark grey droplet contains ions I (e.g. $K^+$).
Figure 4B:
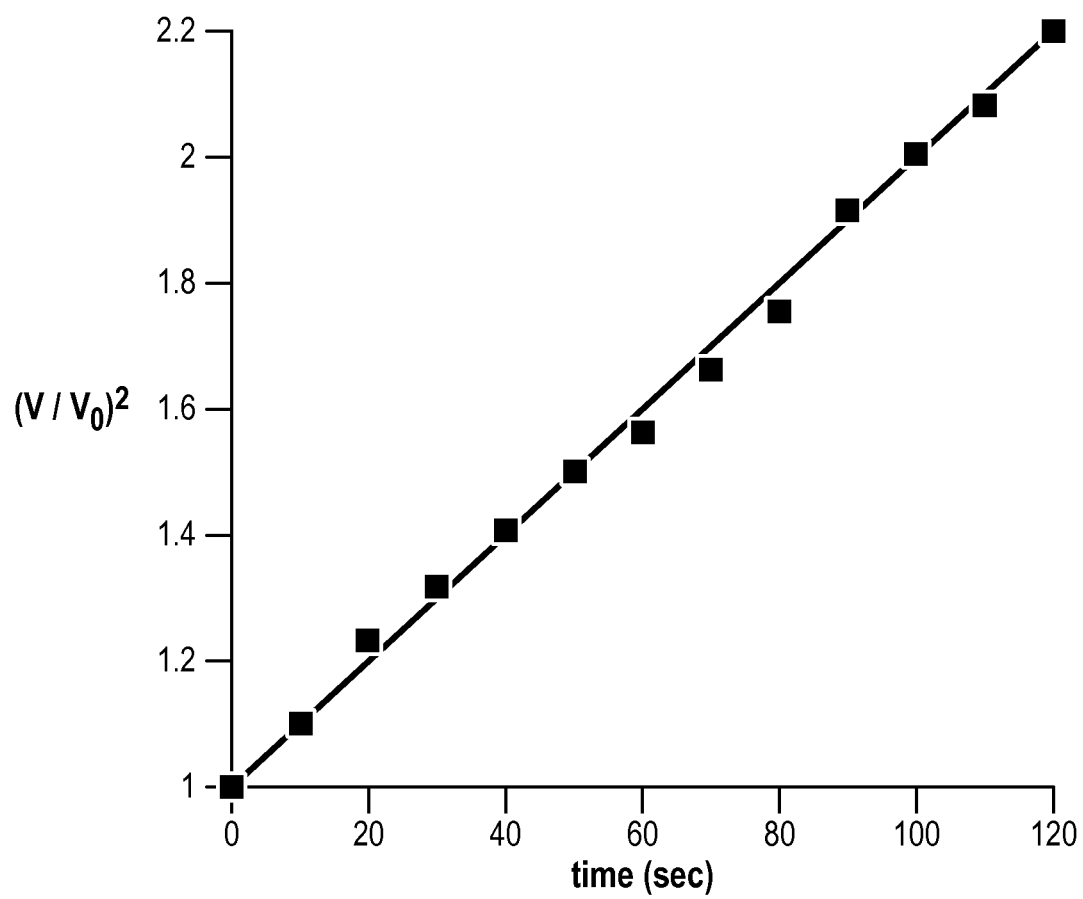
FIG. 4b illustrates the evolution of the square of $V_2/V_0$ where $V_2$ is the droplet volume and $V_0$ is the initial droplet volume of $D_2$ where $c_2>c_1$ (i.e. at t=0) in function of time in the case where the ion channels (3) are inactive. Permeation of water exclusively occurs through the bilayer, which has a signature of a linear increase of square of the drop volume over time.

The behaviour of two aqueous droplets having distinct concentration of ions I ($K^+$) in a hydrophobic medium (silicon oil+chloroform) after contacting is also presented in Thiam et al. 2012, the content of which is incorporated by reference herein. The evolution of the size of the droplets is illustrated on FIGS. 4a and 4b. The use of a mixture of triglycerides and hydrocarbon (such as soybean oil/squalene) as hydrophobic medium, in comparison to the use of a mixture of silicon oil and chloroform in Thiam et al. 2012, allows a better stability of the droplets without using chloroform which could be detrimental in the presence of the ion channels.

2. Example with Active Ion Channels

The experiment of example 1 was repeated with the presence of ion channels in the DIBs, and more particularly the following ion channels: Kv1.5 (0.01 mg/ml) and Alpha haemolysin (0.02 mg/ml) respectively.

Alpha haemolysin is soluble in the aqueous phase and thus the ion channels were directly added in the aqueous phase (the one formed with $MgCl_2$) used to generate the $D_2$ droplets.

Kv1.5 channels are not soluble in the aqueous phase and thus were bound to DPhPC (diphytanoylphosphatidylcholine) liposomes as described below.

Synthesis of the Human Kv1.5 and proteo-liposomes preparation:

Human Kv1.5 channel (gene ID: NM_002234.3) 1.843 kb cDNAs was subcloned into pIVEX 2.4a plasmid (Roche Applied Science, Germany) between NcoI and XhoI restriction sites. This construction encodes the Kv1.5 channel with 6 Histidine tag amino acids upstream of the first methionine. RNA transcription and protein translation were performed in a reaction volume of 2 mL as described by Schwartz et al. 2007, using ribosomes of *E. coli*, 16 µg/mL plasmid and 0.9 mM Brij® 35 detergent. The cell free synthesis reaction mixture was then purified using a NiNTA column eluted with 300 mM imidazole and 0.09 mM Brij® 35. In order to prepare the proteo-liposomes, 0.05 mg of freshly purified Kv1.5 and 1 mg DPhPC liposome (protein/lipid ratio=1/5000) were mixed using 23 mM Octyl Glucoside (OG) detergent for 10 min. at 4° C. This OG concentration results in an isotropic solution of mixed phospholipid-protein-detergent micelles; the proteins spontaneously associate with the lipids to form proteo-liposomes containing OG. The detergent was then removed by dialysis using MIDI GeBa flex-tube (MWCO 3.5 kDa) in a 1 L buffer containing 1 g biobeads (Biorad, USA).

The proteo-liposomes were then added in the aqueous phase (the one formed with KCl) used to generate the $D_2$ droplets. Prior to the mixing of the two emulsions, the $D_2$ droplets containing the proteo-liposomes were thoroughly vortexed in the oil solution; in microfluidics, this step is achieved by forming the droplets in the oil and flowing them in a zig-zag array. This step allows exploding the proteo-liposomes to the oil-water interface and relocating the proteins (ion channels) at the oil-water interface. For Alpha haemolysin, this step was not necessary.

The proteins (Kv1.5 or Alpha haemolysin ion channels) were located in the DIB bilayer and allow $K^+$ (for Kv1.5) or $Cl^-$ (for Alpha haemolysin) ion flux establishment in a direction opposite to the water flux, which goes from $D_1$ to $D_2$ droplets. After one hour, we assumed equilibrium was reached, $D_1$-$DS_2$ adhering droplets reached equi-osmolarity and were still visible with no substantial change in their initial size.

3. Example with Active Ion Channels Using a Microfluidic Device

Figure 7:
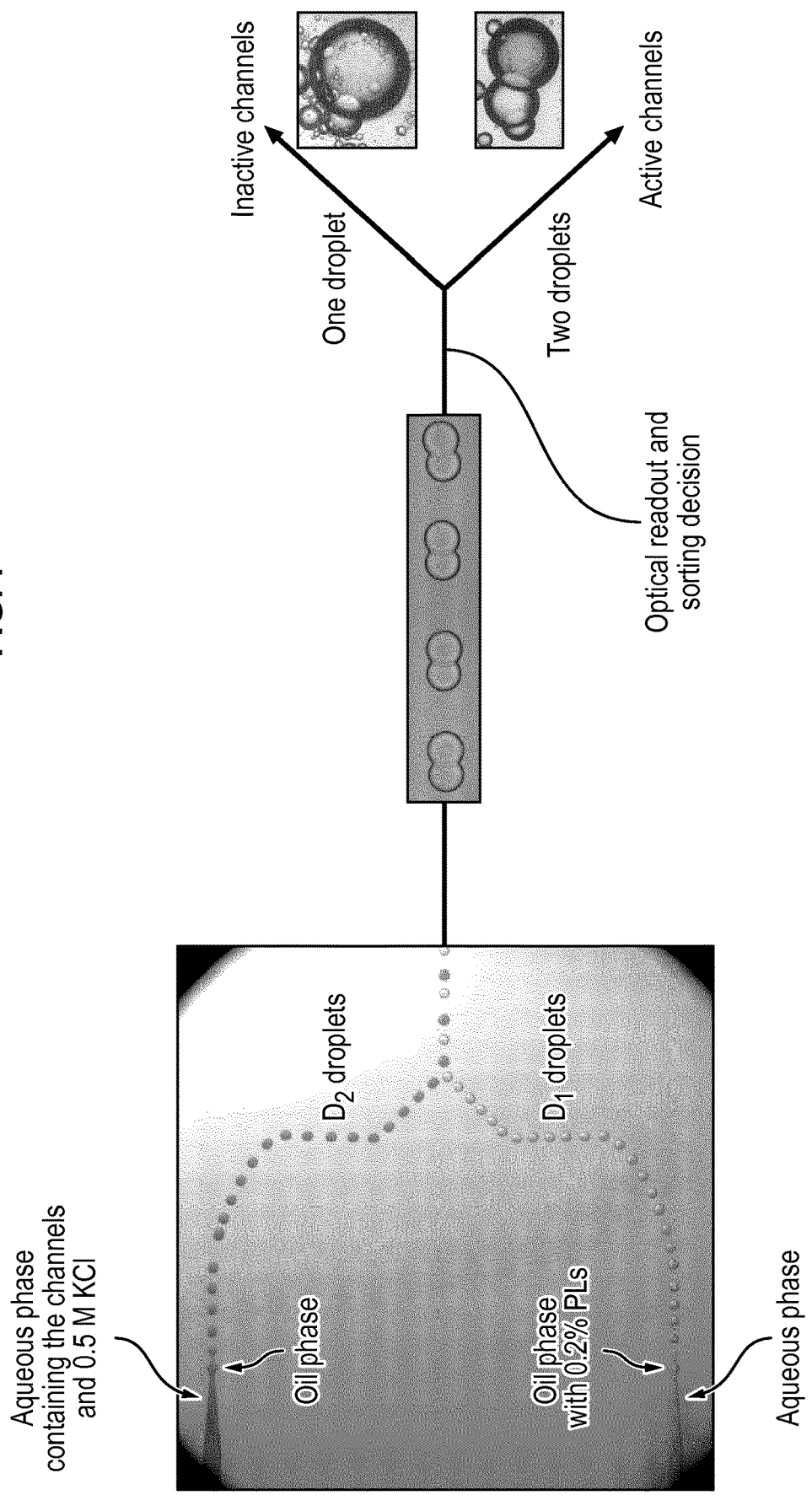
FIG. 7 illustrates the formation of pairs of $D_1/D_2$ ($c_1<c_2$) droplets in the case of the use of Kv1.5 channels in a continuous manner thanks to a microfluidic device. The $K^+$ ions are moving from $D_2$ to $D_1$ through the active Kv1.5 channels until the isosmotic concentration is reached in both droplets.

FIG. 7 illustrates the formation of pairs of $D_1$/$D_2$ droplets (involving Kv1.5 channels) in a continuous manner thanks to a microfluidic device. $AS_1$ and $AS_2$ aqueous phases and the oil phases are as defined above in the case of Kv1.5 channels, except that the oil phase, where the droplets are formed with $AS_2$ aqueous phase, does not contain phospholipids. A flow of $D_2$ droplets (light grey) in an oil phase and a flow of $D_1$ droplets (dark grey) in another oil phase are formed and meet at the entry of a main channel (here a linear channel) so as to allow the alternate entry of the $D_1$ and $D_2$ droplets which can then be brought into contact, notably by varying the pressure. Pairs of $D_1$ and $D_2$ droplets are thus formed in the main channel and analysed at the end of the main channel (when equilibrium is reached) by optical readout. In the present case, the number of droplets is analysed: one droplet means an inactive channel and will be directed towards a first outlet, whereas two droplets mean an active channel and will be directed towards a second outlet.

REFERENCES

Barriga et al. "Droplet interface bilayer reconstitution and activity measurement of the mechanosensitive channel of large conductance from *Escherichia coli*" 2014, 80(5), 1-4.
Bayley et al. "Droplet interface bilayers" *Mol. Biosyst.* 2008, 1, 1191-1208.
Schwarz et al. "Preparative scale cell-free expression systems: new tools for the large scale preparation of integral membrane proteins for functional and structural studies." *Methods* 2007, 41, 355-369.
Schlicht and Zagnoni "Droplet-interface-bilayer assays in microfluidic passive networks" *Scientific Reports* 2015, 5, 1-8.
Thiam et al. "From Stability to Permeability of Adhesive Emulsion Bilayers" *Langmuir* 2012, 28 (15), 6291-6298.
Villar et al. "Formation of droplet networks that function in aqueous environments" *Nature Nanotechnology* 2011, 6(12), 803-808.
WO 2008/012552
US 2012/0220481
U.S. Pat. No. 8,268,627
U.S. Pat. No. 8,293,339
U.S. Pat. No. 8,506,905

The invention claimed is:

1. A method to analyze the activity of an ion channel comprising:
   (i) providing in a hydrophobic medium a first droplet $D_1$ of an aqueous solution $AS_1$ comprising a concentration $c_1$ of an ion I with $c_1 \geq 0$, wherein the droplet $D_1$ is surrounded by a monolayer of amphiphilic molecules,
   (ii) (ii) providing in the said hydrophobic medium a second droplet $D_2$ of an aqueous solution $AS_2$ comprising a concentration $c_2$ of the ion I with $c_2 \geq 0$ and $c_2 \neq c_1$, wherein the droplet $D_2$ is surrounded by a monolayer of amphiphilic molecules further comprising the ion channels to be analyzed,
   (iii) (iii) bringing the first droplet $D_1$ and the second droplet $D_2$ into contact so as to form a bilayer of amphiphilic molecules in the contact area, wherein the bilayer of amphiphilic molecules further comprises ion channels to be analyzed, and measuring the radius of the two droplets when they are brought into contact referred to as initial state, and
   (iv) (iv) maintaining the first droplet $D_1$ and the second droplet $D_2$ into contact until equilibrium is reached, wherein at equilibrium the size of the two droplets does not evolve anymore and the osmolarity between the two droplets is in equilibrium;
      and measuring the radius of the two contacted droplets or determining the number of resulting droplet(s) at the equilibrium referred to as equilibrium state,
   wherein the ion channel is inactive when the difference of the radius of at least one droplet between its initial state and its equilibrium state is at least 10% or when only one droplet is obtained at the equilibrium state.

2. The method according to claim 1, wherein the ion channel is a sodium channel, a potassium channel, a calcium channel, a proton channel or a chloride channel and the ion I is $Na^+$, $K^+$, $Ca^{2+}$, $H^+$ or $Cl^-$ respectively.

3. The method according to claim 1, wherein the hydrophobic medium is an oil; triglycerides; silicone oil; a hydrocarbon; or a mixture thereof.

4. The method according to claim 1, wherein the amphiphilic molecules are phospholipids, glycolipids, cholesterol, or a mixture thereof.

5. The method according to claim 4, wherein the amphiphilic molecules are phospholipids.

6. The method according to claim 5, wherein the amphiphilic molecules are selected from dioleoylphosphatidylcholine (DOPC), dipalmitoylphosphatidylcholine (DPPC), dioleoylphosphatidylethanolamine (DOPE), dioleoylphosphatidylserine (DOPS), dioleoylphosphatidylglycerol (DOPG), and mixtures thereof.

7. The method according to claim 1, wherein the first and second droplets $D_1$ and $D_2$ have a diameter comprised between 0.5 μm and 1000 μm.

8. The method according to claim 1, wherein the concentration $c_1$ or $c_2$ is 0 or the concentrations $c_1$ and $c_2$ satisfy the following equation:

$$|c_1-c_2|/(c_1+c_2) > 0.1.$$

9. The method according to claim 1, wherein the higher concentration of $c_1$ and $c_2$ is comprised between 1 mM and 1 M.

10. The method according to claim 1, wherein step (i) is performed by:
    providing the aqueous solution $AS_1$,
    providing the hydrophobic medium further containing the amphiphilic molecules, and
    forming a droplet of the aqueous solution $AS_1$ in the hydrophobic medium in which the amphiphilic molecules are present.

11. The method according to claim 1, wherein the ion channels are soluble in the aqueous solution $AS_2$ and step (ii) is performed by:
    providing the aqueous solution $AS_2$ further containing the ion channels,
    providing the hydrophobic medium further containing the amphiphilic molecules, and
    forming a droplet of the aqueous solution $AS_2$ which contains the ion channels in the hydrophobic medium which contains the amphiphilic molecules.

12. The method according to claim 1, wherein step (ii) is performed by:
    providing the aqueous solution $AS_2$ further containing the ion channels present in liposomes,
    forming a droplet of the aqueous solution $AS_2$ which contains the ion channels (3) present in liposomes in the hydrophobic medium containing no amphiphilic molecule,
    shaking the droplet thus formed, and
    adding the amphiphilic molecules to the hydrophobic medium.

13. The method according to claim 1, wherein the radius of the droplets is measured by means of an optical detection device.

14. The method according to claim 1, used in high-throughput.

15. The method according to claim 1, performed by means of a microfluidic analysis system comprising:
    a microfluidic device comprising:
      a main microfluidic channel comprising one inlet and one outlet, through which alternate droplets $D_1$ and $D_2$ can flow in the hydrophobic medium from the inlet to the outlet of the microfluidic channel, at least two outlets connected to the outlet of the main microfluidic channel and wherein:

the first outlet of the microfluidic device is further connected to a first receiver container intended to receive the droplets analyzed as containing active ion channels, and the second outlet of the microfluidic device is further connected to a second receiver container intended to receive the droplets analyzed as containing inactive ion channels, at least four inlets connected to the inlet of the main microfluidic channel and wherein:

the first two inlets of the microfluidic device are further connected respectively to a reservoir intended to contain the aqueous solution $AS_1$ and to a reservoir intended to contain the hydrophobic medium and the amphiphilic molecules, and the last two inlets are further connected respectively to a reservoir intended to contain the aqueous solution $AS_2$ and the ion channels optionally present in liposomes and to a reservoir intended to contain the hydrophobic medium and optionally the amphiphilic molecules, wherein, when the ion channels are present in the aqueous solution $AS_2$ in liposomes, the microfluidic device comprises a fifth inlet connected to the inlet of the main microfluidic channel and to a reservoir intended to contain the amphiphilic molecules and optionally the hydrophobic medium, at least three reservoirs adapted for containing respectively (i) the aqueous solution $AS_1$, (ii) the aqueous solution $AS_2$ and the ion channels optionally present in liposomes, and (iii) the hydrophobic medium and/or the amphiphilic molecules, at least two receiver containers adapted for receiving respectively (i) the droplets analyzed as containing active ion channels, and (ii) the droplets analyzed as containing inactive ion channels, and a detection device placed at the end of the main microfluidic channel.

16. The method according to claim 3, wherein the hydrophobic medium is a mixture of triglycerides and hydrocarbon.

17. The method according to claim 5, wherein the phospholipids are phosphatidylcholines (PC), phosphatidylethanolamines (PE) or a mixture thereof.

18. The method according to claim 6, wherein the amphiphilic molecules are selected from DOPC, DOPE and mixtures thereof.

19. The method according to claim 7, wherein the first and second droplets $D_1$ and $D_2$ have a diameter comprised between 50 µm and 200 µm.

20. The method according to claim 14, used in a high-throughput screening.

* * * * *

UNITED STATES PATENT AND TRADEMARK OFFICE
CERTIFICATE OF CORRECTION

PATENT NO. : 10,690,680 B2
APPLICATION NO. : 15/776685
DATED : June 23, 2020
INVENTOR(S) : Thiam et al.

Page 1 of 1

It is certified that error appears in the above-identified patent and that said Letters Patent is hereby corrected as shown below:

In the Claims

Claim 12, Column 18, Line 50, delete "(3)".

Signed and Sealed this
Second Day of August, 2022

Katherine Kelly Vidal
*Director of the United States Patent and Trademark Office*